(12) United States Patent
Spinelli et al.

(10) Patent No.: US 7,346,393 B2
(45) Date of Patent: Mar. 18, 2008

(54) IMPLANTABLE CARDIAC RHYTHM MANAGEMENT SYSTEM HAVING MULTIPLE THERAPY MODALITIES

(75) Inventors: Julio Spinelli, Shoreview, MN (US); Qingsheng Zhu, Little Canada, MN (US); Bruce H. Kenknight, Maple Grove, MN (US); Yinghong Yu, Maplewood, MN (US); Jiang Ding, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 408 days.

(21) Appl. No.: 10/460,975

(22) Filed: Jun. 12, 2003

(65) Prior Publication Data

US 2004/0254614 A1 Dec. 16, 2004

(51) Int. Cl.
*A61N 1/36* (2006.01)
(52) U.S. Cl. .............................. 607/9; 607/14; 607/25
(58) Field of Classification Search ............... 607/4–28
See application file for complete search history.

(56) References Cited

U.S. PATENT DOCUMENTS

| | | | |
|---|---|---|---|
| 5,792,203 A | | 8/1998 | Schroeppel |
| 6,185,459 B1 | | 2/2001 | Mehra et al. |
| 6,272,377 B1 * | | 8/2001 | Sweeney et al. ............ 600/515 |
| 6,280,389 B1 | | 8/2001 | Ding et al. |
| 6,635,048 B1 * | | 10/2003 | Ullestad et al. .......... 604/890.1 |
| 6,766,189 B2 * | | 7/2004 | Yu et al. .................... 600/510 |
| 2002/0082653 A1 | | 6/2002 | Stahmann et al. |
| 2002/0082656 A1 | | 6/2002 | Stahmann et al. |
| 2002/0082660 A1 * | | 6/2002 | Stahmann et al. ............ 607/14 |
| 2002/0143264 A1 | | 10/2002 | Ding et al. |
| 2002/0161307 A1 | | 10/2002 | Yu et al. |
| 2003/0083709 A1 | | 5/2003 | Zhu et al. |
| 2004/0147966 A1 * | | 7/2004 | Ding et al. .................... 607/9 |
| 2004/0215257 A1 * | | 10/2004 | Van Oort et al. ............... 607/9 |

OTHER PUBLICATIONS

Auricchio et al. "Effect of Paching Chamber and Atrioventricular Delay on Acute Systolic Function of Paced Patients with Congestive Heart Failure." Circulation. 1999; 99: 2993-3001.*
Kass et al. "Improved Left Ventricular Mechanics from Acute VDD Pacing in Patients with Dilated Cardiomyopathy and Ventricular Conduction Delay." Circulation. 1999; 99: 1567-1573.*

* cited by examiner

*Primary Examiner*—Angela D. Sykes
*Assistant Examiner*—Rex Holmes
(74) *Attorney, Agent, or Firm*—Schwegman, Lundberg & Woessner, P.A.

(57) ABSTRACT

A cardiac rhythm management system for providing a plurality of therapy modalities. For example, the system may include a cardiac resynchronization therapy module for providing cardiac resynchronization therapy and a pacemaker module for providing bradycardia therapy, as well as a selector module coupled to the cardiac resynchronization therapy module and the bradycardia module. The selector module may select an operating mode from among a plurality of operating modes including the cardiac resynchronization therapy module and the pacemaker module. Various manual and automatic methods may be used to select the operating mode. In addition, a reversion management system may be included to assist the cardiac rhythm management system to recover in case of a disruption to the system.

27 Claims, 8 Drawing Sheets

IMPLANTABLE CARDIAC RHYTHM MANAGEMENT SYSTEM HAVING MULTIPLE THERAPY MODALITIES

TECHNICAL FIELD

This invention relates to a cardiac rhythm management system. In addition, the invention relates to an implantable cardiac rhythm management system having multiple therapy modalities. Further, the invention relates to a cardiac rhythm management system including at least bradycardia therapy and cardiac resynchronization therapy capabilities.

BACKGROUND

Numerous therapies have been developed to address the needs of individuals suffering from heart diseases or abnormalities. For a first example, individuals suffering from bradycardia, or an abnormally slow heart rate, can be treated using a pacemaker. A pacemaker alters the individual's heart rate to return heart rate performance to normal levels. A pacemaker typically accomplishes this by delivering a series of electrical impulses to the heart tissue via one or more leads, thereby stimulating the heart tissue to contract at a specified rate. Therefore, a primary function of bradycardia therapy using a pacemaker is to provide rate support for the heart.

The pacemaker typically functions as an on-demand device, meaning that the pacemaker will function only when rate support is necessary. The pacemaker will typically delay for a certain duration, termed an escape interval, before providing an electrical impulse to the heart. If the intrinsic electrical activity of the individual's heart causes the heart to contract before the escape interval expires, the pacemaker will not send an electrical impulse. Instead, the pacemaker will reset the escape interval and wait for the escape interval to expire again. Therefore, if the individual's heart is beating at a specified acceptable rate, the pacemaker will not provide an electrical impulse until rate support is needed. Other functions of a pacemaker may include adaptive-rate pacing, in which the rate of the pacing is increased or decreased based on an individual's physiological needs.

In a second example of a heart abnormality, individuals may exhibit a decrease in hemodynamic efficiency due to the onset of congestive heart failure (CHF). A possible therapy for CHF is the use of a cardiac resynchronization therapy (CRT) device. A CRT device, like a pacemaker, can deliver a series of electrical impulses to a heart tissue. However, a CRT device functions to synchronize the contraction of a heart rather than to pace the heart like a pacemaker. A CRT device may deliver a series of electrical impulses to the heart at a set rate, usually in conjunction with each intrinsic heartbeat, to synchronize the contraction of different sections of the heart. Research and development into the use of a CRT device to treat CHF has established a set of therapeutic features that can be customized for each individual in order to maximize hemodynamic function. For instance, methods have been developed for optimizing the timing between electrical stimuli, thereby providing maximum resynchronization benefits. Therefore, a primary function of a CRT device is resynchronization, making the timing and the delivery of each electrical impulse for each heartbeat important.

Consequently, while bradycardia therapy focuses on rate support on an as-needed basis, CHF therapy focuses on resynchronization. During resynchronization, particular attention may be paid to atrioventricular delays, and electrical impulses are typically provided for every heartbeat. Because therapeutic priorities of bradycardia patients differ from those of CHF patients, it is a current practice in the industry to design different products for a patient depending on whether a patient exhibits bradycardia or CHF. Therefore, initial decisions must be made for each patient on whether to implant a bradycardia pacemaker or a CHF cardiac resynchronization therapy device.

Currently, pacemakers and CRT devices are not interchangeable, and a pacemaker cannot be reprogrammed to be a CRT device and vice versa. Therefore, not only must treatment decisions be made initially, once a device is implanted into the patient, it cannot be adapted should the patient's needs change, such as, for example, from a need for bradycardia therapy to a need for cardiac resynchronization therapy. Further, product development costs are increased because separate devices must be designed.

It would therefore be desirable to develop a cardiac rhythm management system having multiple therapy modalities.

SUMMARY

Generally, the present invention relates to a cardiac rhythm management system. In addition, the invention relates to an implantable cardiac rhythm management system having multiple therapy modalities. Further, the invention relates to a cardiac rhythm management system including at least bradycardia therapy and cardiac resynchronization therapy capabilities.

In one aspect, the invention relates to a cardiac rhythm management system including a cardiac resynchronization therapy module for providing cardiac resynchronization therapy, a pacemaker module for providing bradycardia therapy, and a selector module coupled to the cardiac resynchronization therapy module and the pacemaker module, wherein the selector module selects an operating mode from among a plurality of operating modes including the cardiac resynchronization therapy module and the pacemaker module.

In another aspect, the invention relates to a method for a cardiac rhythm management system to select between a plurality of operating modes, the method including: detecting physiological data of an individual; and selecting an operating mode from the plurality of modes for the cardiac rhythm management system based on the physiological parameter.

In yet another aspect, the invention relates to a cardiac rhythm management device including means for providing a first operating mode associated with a first therapy for a heart, means for providing a second operating mode associated with a second therapy for the heart, and means for selecting between the first operating mode and the second operating mode.

The above summary of the present invention is not intended to describe each disclosed embodiment or every implementation of the present invention. The figures and the detailed description which follow more particularly exemplify these embodiments.

DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention relates to a cardiac rhythm management system. In addition, the invention relates to an implantable cardiac rhythm management system having multiple therapy modalities. Further, the invention relates to a cardiac rhythm management system including at least bradycardia therapy and cardiac resynchronization therapy capabilities. While the present invention is not so limited, an appreciation of various aspects of the invention will be gained through a discussion of the examples provided below.

The present apparatus and methods are described with respect to implantable cardiac rhythm management (CRM) systems, such as pacemakers, cardioverter/defibrillators, pacer/defibrillators, and multi-chamber and/or multi-site (in single or multiple heart chambers) cardiac resynchronization therapy (CRT) devices. Such CRT devices are included within CRM systems even though the CRT devices need not necessarily modulate heart rate. Such CRT devices may instead provide contraction-evoking stimulations that establish or modify the conduction path of propagating depolarizations to obtain more efficient pumping of the heart. Moreover, the present apparatus and methods also find application in other implantable medical devices and in devices that may not be implanted including, but not limited to, external pacemakers, cardioverter/defibrillators, pacer/defibrillators, multi-chamber and/or multi-site CRT devices, monitors, programmers, and recorders, whether such devices are used for providing diagnostics, therapy, or both.

Example CRM systems and methods are described below. The systems and methods provided are examples only, and other systems and methods can also be used.

I. Example CRM System

A. Components of the CRM System

Figure 1:
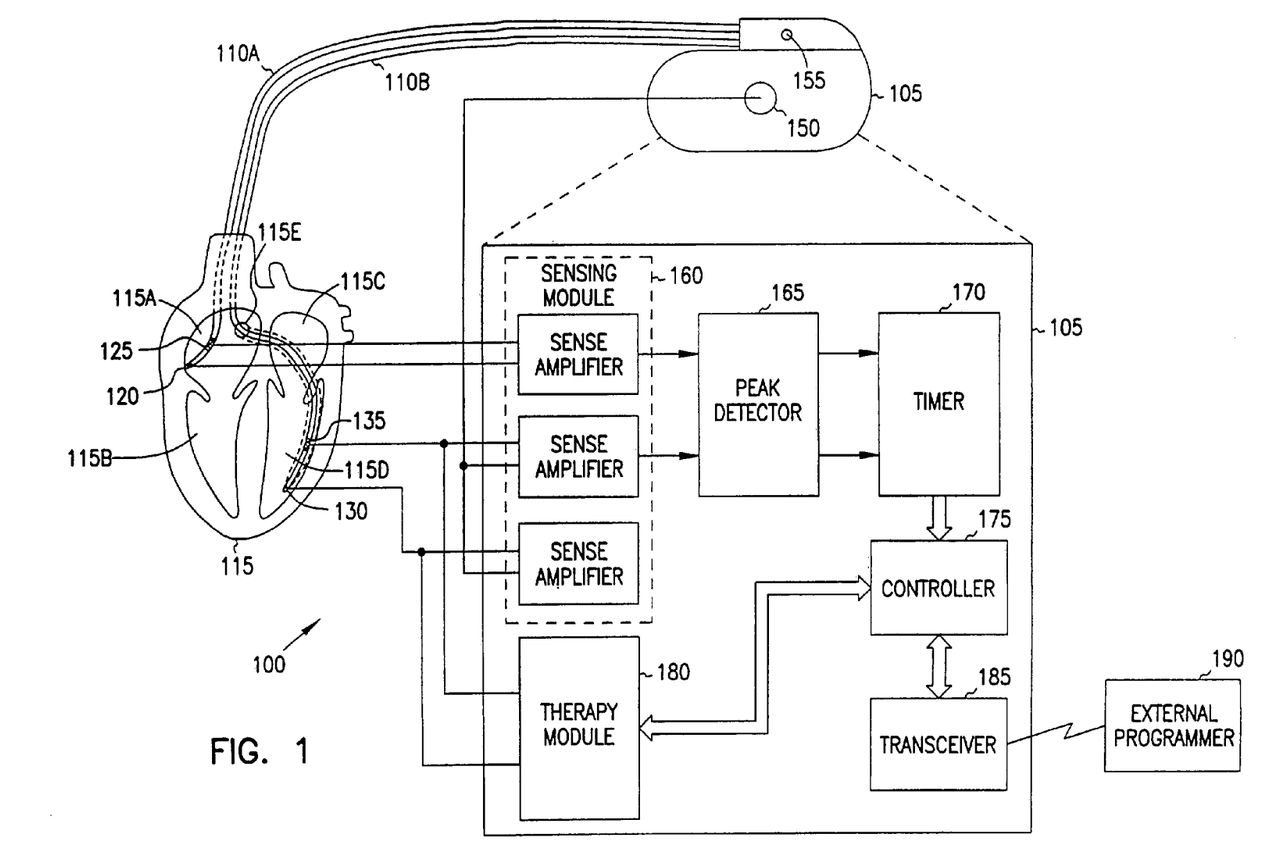
FIG. 1 is a schematic/block diagram illustrating one example embodiment of a cardiac rhythm management system coupled to a heart in accordance with the present invention.

FIG. 1 is a schematic/block diagram illustrating one example embodiment of a CRM system 100 coupled to a heart 115. In this embodiment, system 100 includes, among other components, a CRM device 105 that is coupled by leads 110A-B to the heart 115. The heart 115 includes four chambers: a right atrium 115A, a right ventricle 115B, a left atrium 115C, and a left ventricle 115D. The heart 115 also includes a coronary sinus 115E, a vessel that extends from the right atrium 115A toward the left ventricular free wall.

In one embodiment, the lead 110A includes an electrode associated with the right atrium 115A, such as tip electrode 120 and/or ring electrode 125. The electrode is "associated" with the particular heart chamber by inserting it into that heart chamber, or by inserting it into a portion of the heart's vasculature that is close to that heart chamber, or by epicardially placing the electrode outside that heart chamber, or by any other technique of configuring and situating an electrode for sensing signals and/or providing therapy with respect to that heart chamber. Lead 110B, which is introduced into the coronary sinus 115E and/or the great cardiac vein or one of its tributaries, includes one or more electrodes associated with the left ventricle 115D, such as electrodes 130 and 135. The device 105 may also include other electrodes, such as housing electrode 150 and/or header electrode 155, which are useful for, among other things, unipolar sensing of heart signals or unipolar delivery of contraction-evoking stimulations in conjunction with one or more of the electrodes 120, 125, 130, and 135 associated with the heart 115. Alternatively, bipolar sensing and/or therapy may be used between electrodes 120 and 125, between electrodes 130 and 135, or between one of electrodes 130 and 135 and another closely situated electrode.

Figure 2:
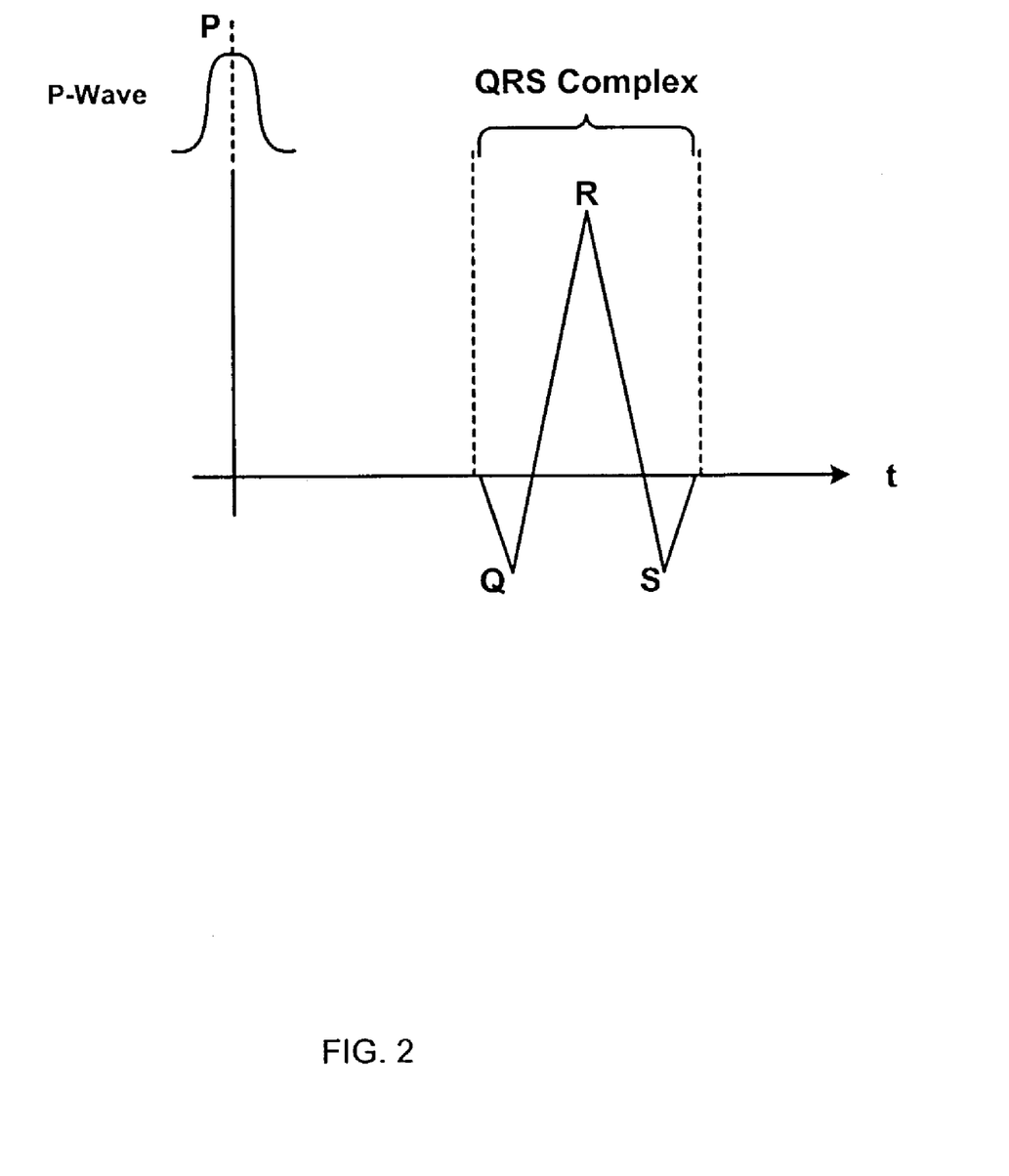
FIG. 2 is a graph showing atrial and ventricular depolarization as a function of time.

The CRM device 105 includes a sensing module 160 that is coupled to one or more of the electrodes for sensing electrical depolarizations corresponding to heart chamber contractions. Such electrical depolarizations of the heart tissue include atrial depolarizations, referred to as P-waves, and ventricular depolarizations, referred to as QRS complexes. The QRS complex is a rapid sequence of several signal excursions away from a baseline in sequentially switching polarity, with the largest excursion referred to as an R-wave. See FIG. 2, showing a graph of atrial and ventricular depolarizations.

A peak detector 165 is coupled to sensing module 160 for detecting the P-wave peak from the right atrium 115A, obtained by bipolar sensing between electrodes 120 and 125 or by any other sensing technique. The peak detector 165 also senses the R-wave peak at a plurality of different sites associated with the left ventricle 115D, such as at each of the electrodes 130 and 135. In one example, the electrode 130 is located near the left ventricular apex and the electrode 135 is located near the left ventricular base regions, i.e., closer to the left atrium 115C.

In another example, one of the two electrodes 130 and 135 (or an additional third electrode) is located in a middle portion ("midregion") of the left ventricle 115D between the left ventricular apex and the left ventricular base region. In another example, the electrodes 130 and 135 are located in a middle cardiac vein closer to a wall of the ventricle. Sensing at the electrodes 130 and 135 is either unipolar (e.g., the electrode 130 and/or 135 is sensed in combination with a relatively distant electrode, such as one or both of housing electrode 150 and/or header electrode 155) or bipolar (e.g., the electrode 130 and/or 135 is sensed in combination with another relatively close electrode, such as another electrode disposed on the lead 110B and associated with the left ventricle 115D, or another electrode disposed on the lead 110A and associated with the right atrium 115A).

The system 100 may also include a telemetry transceiver 185 disposed in the device 105, which is communicatively coupled to an external programmer 190. A time module 170 may also be included to measure a time duration between various events, such as, for example, the duration of time between adjacent contractions of the heart 115.

The system 100 includes multiple therapy modalities. For example, as discussed below, the system 100 may provide both bradycardia therapy ("pacemaker mode"), as well as cardiac resynchronization therapy ("CRT mode"). The mode in which the system 100 is currently operating is termed the "operating mode." Although the example embodiments illustrate two therapy modalities, other therapy modalities may also be provided.

A controller 175 is provided to select an operating mode from among the multiple therapy modalities. The controller 175 may select the operating mode using one or more of the methods described below. Once selected, the controller 175 communicates the operating mode to a therapy module 180.

The therapy module 180 is coupled to electrodes 130 and 135 for delivery of a desired therapy modality, specifically the therapy modality associated with the selected operating mode, to the heart 115. The therapy module 180 is configured to deliver the desired therapy modality using a plurality of operating parameters, as described below.

B. Reuse of Operating Parameters

The operating mode for the system may be selected using both automatic and manual methods, as disclosed below. Correct selection of the operating mode can be important for several reasons, including that operating parameters associated with the different operating modes, as well as the goals of the therapies associated with each operating mode, may differ significantly. An "operating parameter" is a configuration variable associated with a specific aspect of a given therapy controlling how the CRM device functions. For example, an operating parameter may include a stimulation and sensing configuration such as "VDD," which is a standard industry convention for cardiac rhythm management systems. See, e.g., U.S. Pat. No. 5,792,203 to Schroeppel. Although the two example therapy modalities provided in the embodiment disclosed herein share some of the same operating parameters and are implemented as a single system, differences exist.

For example, Table 1 provided below illustrates some of the differences for several operating parameters associated with pacemakers and CRT devices, as are well known to those of ordinary skill in the art.

TABLE 1

Typical Operating Parameters Associated with Example Operating Modes

| Parameter | Bradycardia-Pacemaker | CHF-CRT Device |
|---|---|---|
| Stimulation/Sensing Mode | DDD(R) | VDD |
| LRL | 60 ppm | 40 ppm |
| Noise Response | DOO | inhibit |
| Atrioventricular Delay | 120 ms | 100 ms |

As Table 1 illustrates, the operating parameters associated with different therapies may vary significantly. For example, if the device is operating in CRT mode, the device may include operating parameters requiring the device to inhibit the delivery of electrical impulses (i.e., Noise Response=inhibit) if interference causes the device to lose atrial sensing, rather than to deliver electrical impulses asynchronously, as this may decrease hemodynamic performance. On the other hand, if the device is operating in pacemaker mode, the device may include operating parameters requiring the device to continue to deliver electrical impulses (i.e., Noise Response="DOO" mode) asynchronously. Because selection of the incorrect operating mode can actually decrease hemodynamic performance, it is important to correctly determine which therapy is appropriate for each patient.

Figure 3:
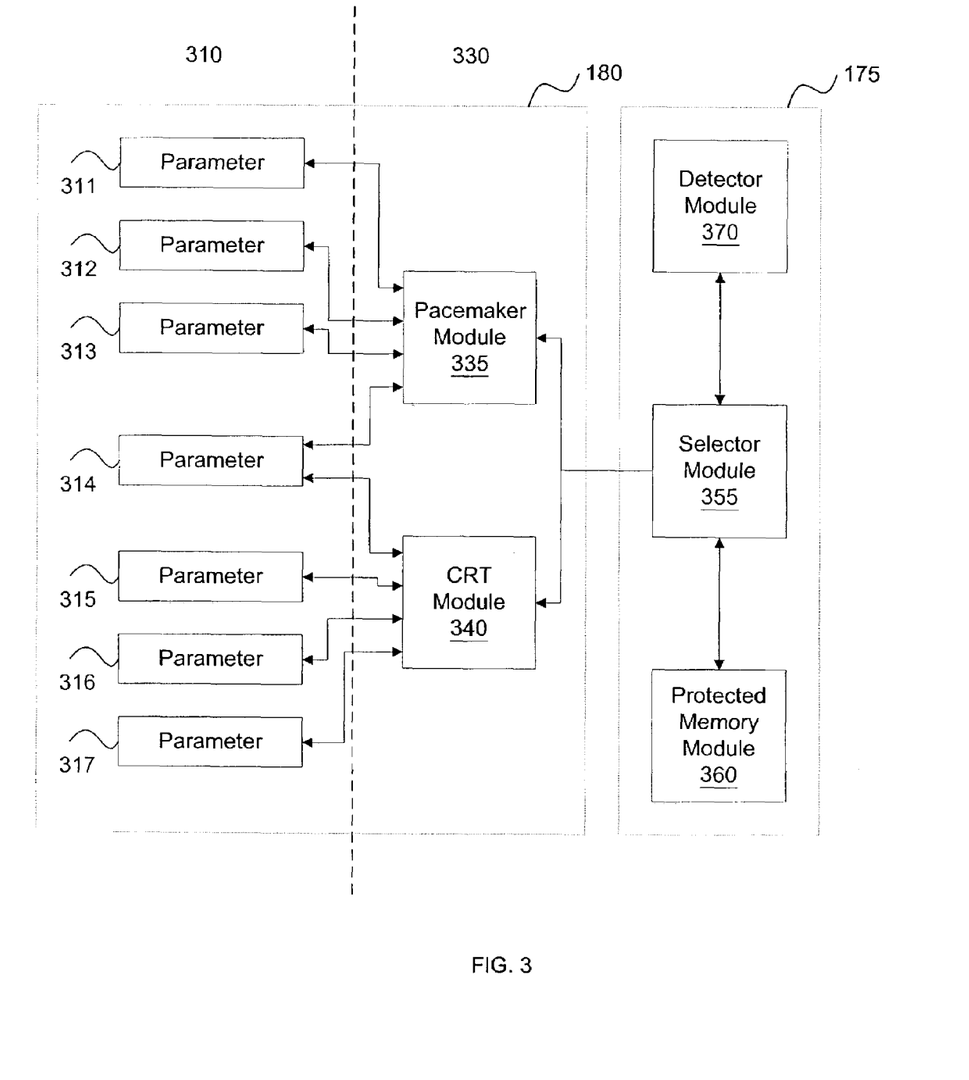
FIG. 3 illustrates a plurality of modules associated with an example cardiac rhythm management system made in accordance with the present invention.

Whenever possible, operating parameters that are common between a CRT mode and a pacemaker mode are shared. As shown in FIG. 3, the example controller 175 and therapy module 180 are illustrated in greater detail. The therapy module 180 includes a pacemaker module 335, a CRT module 340, and operating parameters 311-317 associated with the modules 335 and 340. The controller 175 includes an operating mode selector module 355 coupled to the modules 335 and 340, as well as a protected memory module 360 and a detector module 370, both coupled to the operating mode selector module 355.

The pacemaker module 335 in this example embodiment is associated with the plurality of operating parameters 311-314. The CRT module 340 includes the plurality of operating parameters 314-317. The operating parameter 314 is common to both the pacemaker module 335 and the CRT module 340 and therefore is shared. However, other operating parameters that are not common between the two modules 335 and 340 are maintained separately to avoid conflicts. For example, the operating parameters provided in Table 1 differ and therefore are not shared between the different modes. Further, other operating parameters may be specific to one mode and therefore would not be shared. For example, operating parameters associated with implementing hysterisis may be relevant for pacemaker mode but may not be relevant for CRT mode requiring stimulation at regular intervals. However, other parameters, such as stimulation amplitude and width, P- and R-wave sensing sensitivity, antitachycardia response parameters, etc., may be common to both modes.

C. Configuration of the CRM System

The therapy module 180 of FIG. 3 is further divided into two hierarchical program levels to illustrate the programmable capabilities of the cardiac rhythm management system 100. Additionally illustrated in FIG. 3 are lower program level 310 and higher program level 330. In order to manually program the system 100, a caregiver may utilize operating mode selector module 355 to select between pacemaker module 335 and CRT module 340. Because this selection is made in the higher program level 330, the caregiver is allowed to simply select between the two modes, and the system 100 automatically uses nominal operating parameters associated with either the pacemaker mode or the CRT mode. For example, if the operating mode selector module 355 is utilized to select pacemaker mode, the associated nominal operating parameters 311-314 are utilized to configure the pacemaker module 335.

However, in some patients the nominal operating parameters will not be sufficient to provide optimal hemodynamic benefits. In these cases, the caregiver may further configure the individual operating parameters associated with an operating mode. These modifications are made in the lower program level 310, in which specific operating parameters associated with the modules 335 and 340 may be configured. For example, if the caregiver utilizes the operating mode selector module 355 to select the pacemaker module 335, the caregiver can configure operating parameters 311-314 to further tailor the pacemaker module 335 to maximize hemodynamic benefits. In this manner, the system 100 may provide ease of use by allowing for selection between the pacemaker module 335 and the CRT module 340 in the higher program level 330, as well as provide for added configurability by allowing for the modification of parameters 311-317 in the lower program level 310.

The operating mode selector module 355 of the controller 175 may further utilize the detector module 370 to automatically select between operating modes. The detector module 370 provides the operating mode selector module 355 with physiological data necessary to implement one or more of the methods described below to automatically select between the two example operating modes. This physiological data may be collected from the patient manually or automatically by the system.

II. Example Methods Used to Select Between the Multiple Therapy Modalities

Selection between the multiple therapy modalities may be automatic or manual. Both automatic (i.e., can be performed by the system 100 without manual intervention) and manual methods for selection of the operating mode are similar in that both may compare a patient's hemodynamic response when operating in various therapy modalities. For example, one or more methods may be used to determine whether the CRM device operating in a first operating mode achieves a better hemodynamic response than when operating in a second operating mode.

Figure 4:
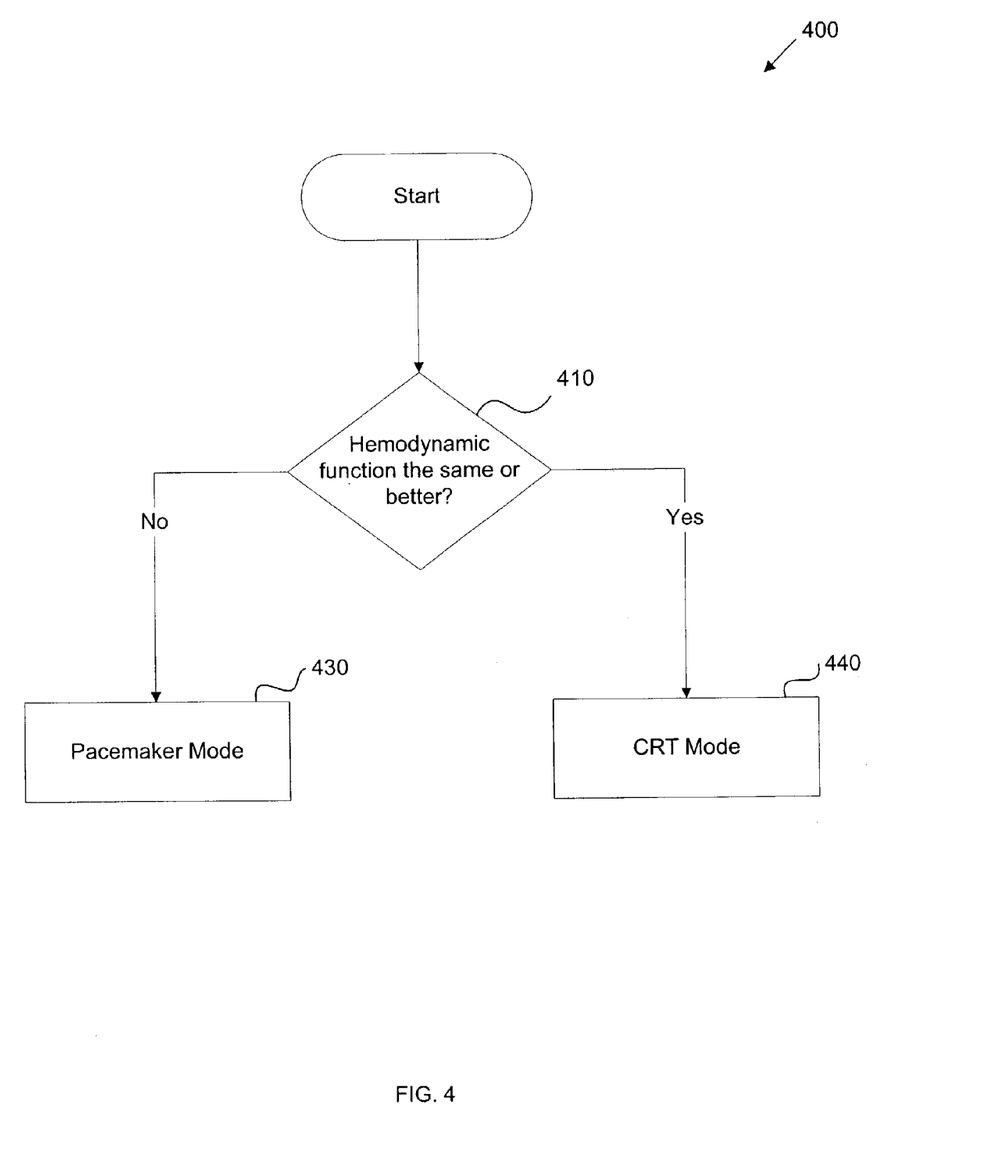
FIG. 4 shows an operational flow of a cardiac rhythm management system according to an embodiment of the present invention.

For example, in the example method illustrated in FIG. 4, a determination is made as to whether the application of cardiac resynchronization therapy would be beneficial to the patient, as shown in operation 410. If the application of cardiac resynchronization therapy would result in the same or an increase in hemodynamic performance, control is passed to operation 440, and the CRM device is placed in CRT mode. Alternatively, if the application of cardiac resynchronization therapy would result in a decrease in hemodynamic performance, then control is passed to operation 430 and the CRM device is placed in pacemaker mode. All of the methods described below for selecting between the two example modes may implement, at some level, the method as shown in FIG. 4.

Figure 5:
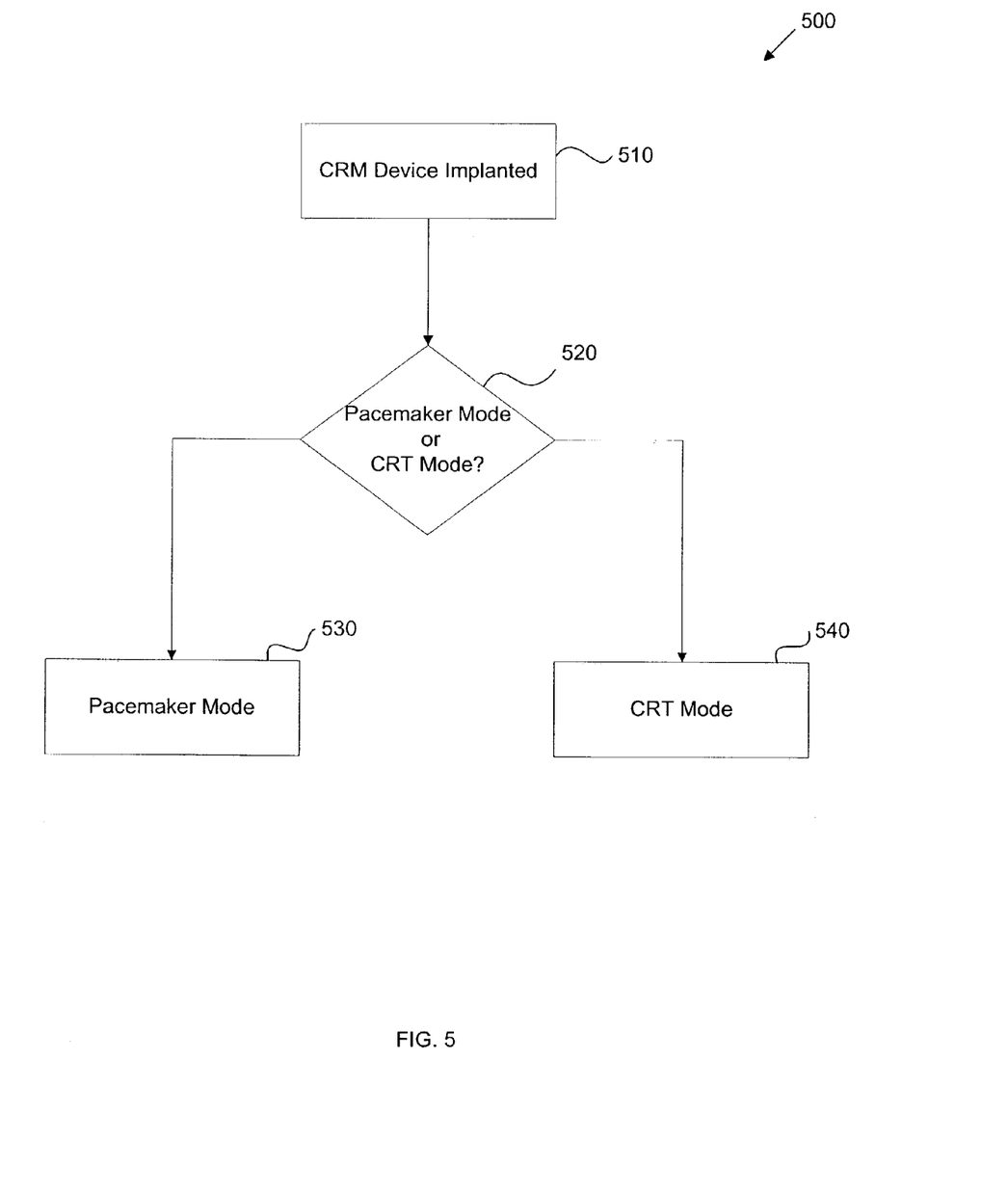
FIG. 5 illustrates an operational flow of a cardiac rhythm management system in accordance with another embodiment of the present invention.

In FIG. 5, an example high-level operational flow 500 is provided for a cardiac rhythm management system such as 100. At operation 510, the system is implanted into a patient using known techniques. In conjunction with, or possibly after implantation, control is passed to operation 520, where a determination is made as to the appropriate therapy to provide to the patient. In the example embodiment, the operation 520 selects between multiple therapy modalities that may be delivered to the patient for treatment of an arrhythmic condition.

In the illustrated method, the therapies include bradycardia therapy (pacemaker mode) and cardiac resynchronization therapy (CRT mode), although other therapies may also be provided. In addition, within each therapy modalities (i.e., the pacemaker mode and the CRT mode), a plurality of sub-therapy modalities can be provided such as, for example, multiple therapies that can be administered to remedy bradycardia.

Selection of the appropriate therapy modality can be achieved manually, using, for example, the external programmer 190 (see, e.g., FIG. 1). Alternatively, the controller 175 may automatically select between pacemaker mode and CRT mode using one or more of the methods described below.

If the therapy modality selected is pacemaker mode, control is passed to operation 530 and the system functions as a state of the art pacemaker with all associated modalities. Alternatively, if the CRT mode is selected, control is passed to operation 540, and the system functions as a state of the art CRT device.

A variety of methods may be used to make the selection in operation 520, as described below.

A. Q*S* Method

In U.S. patent application Ser. No. 10/008,397, filed on Dec. 6, 2001 and entitled "IDENTIFYING HEART FAILURE PATIENTS SUITABLE FOR RESYNCHRONIZATION THERAPY USING QRS COMPLEX WIDTH FROM AN INTRACARDIAC ELECTROGRAM," incorporated by reference herein in its entirety, a method is described for identifying patients who may benefit from cardiac resynchronization therapy through analysis of the duration of ventricular depolarization, or the width of the QRS complex, measured intracardially. According to the method, an intracardiac electrogram is digitalized and smoothed using a rectangular moving window. The time of peak depolarization (R) is determined and the absolute derivative of the waveform is calculated. Next, the maximum absolute derivative before R ("max–BR") and after R ("max–AR") are determined. The Q* point is the first point before R at which the absolute derivative is approximately 2% of max–BR, and the S* is the first point after R at which the absolute derivate is approximately 10% of max–AR. The Q*S* interval is then compared to a threshold value. If the duration is greater than or equal to the threshold, the patient is labeled a responder to cardiac resynchronization therapy and, in operation 520, CRT mode is selected. Alternatively, if the duration is less than the threshold, pacemaker mode may be used. In one embodiment of the method, the threshold is set at approximately 170 milliseconds. Other durations, as well as other threshold values, may also be used.

B. Interval between Q-Wave-LV (Lead) Method

Another method that may be employed to select an operating mode for the CRM device includes measurement of a duration of the onset of ventricular depolarization measured from either a surface ECG or left ventricular intracardiac electrogram to the peak of the left-ventricular intracardiac electrogram at the stimulation site (the "Q-wave-LV interval"). This Q-wave-LV interval is measured, and the duration is compared to a threshold value. If the duration is greater than or equal to the threshold, the stimulation site is labeled a responder site to cardiac resynchronization therapy and CRT mode is selected. Alternatively, if the duration is less than the threshold, pacemaker mode may be used. In one embodiment of the method, the threshold is set at approximately 80 milliseconds if Q is measured from a surface ECG and 100 milliseconds if Q is measured intracardially. Other threshold values may also be used.

C. Surface QRS Wave Method

Another method that may be employed to select an operating mode for the CRM device includes measurement of a duration of ventricular depolarization, or the QRS complex, at the surface of the patient (i.e., intercardially) and comparison of that duration to a threshold value. If the duration is greater than or equal to the threshold, the patient is labeled a responder to cardiac resynchronization therapy and CRT mode is selected. Alternatively, if the duration is less than the threshold, pacemaker mode may be used. In one embodiment of the method, the threshold is set at approximately 150 milliseconds. Other threshold values may also be used.

D. Interventricular Pressure Method

Another method that may be employed to determine a correct operating mode for the system is generally described in U.S. Pat. No. 6,280,389 to Ding et al., incorporated by reference herein in its entirety. This method involves measurement of a patient's left and right ventricular pressure for a specified period of time using a pressure-measuring device. A normalized pressure loop area for each heartbeat measured is then calculated and a mean pressure area determined. This mean pressure area is then compared to a threshold value to determine whether the patient is a responder. If the area is equal to or greater than the threshold, the patient is labeled a responder, and CRT mode is selected. Alternatively, if the area is less than the threshold, pacemaker mode is selected. In an example disclosed in the patent, the threshold is set to 0.3.

E. Paced QRS Method

Another method that may be employed to determine a correct operating mode for a CRM system is generally described in U.S. patent application Ser. No. 09/822,790, filed on Mar. 30, 2001 and entitled "METHOD AND APPARATUS FOR PREDICTING ACUTE RESPONSE TO CARDIAC RESYNCHRONIZATION THERAPY," incorporated by reference herein in its entirety. The method generally described in this application involves measuring a first interval during an intrinsic systolic cycle, measuring a second interval during a stimulation-induced systolic cycle, and comparing a percentage change in duration between the first interval and the second interval against a pre-determined threshold. The interval disclosed is a patient's intrinsic ventricular depolarization, although other intervals may also be used. If the percentage change is equal to or less than the threshold, disclosed as between 10-25 percent, then the patient may be labeled a "responder" and the CRM device may be set to perform in CRT mode. Alternatively, if the percentage change is greater than 10-25 percent, then the CRM device may be set to perform in pacemaker mode.

As previously indicated, the determination made in operation 420 may be automatically made by a CRM system using one or more of the methods described above, or other similar methods. Further, the operating mode may be manually selected by a caregiver and the CRM system manually programmed.

F. Automatic Reconfiguration Method

Figure 6:
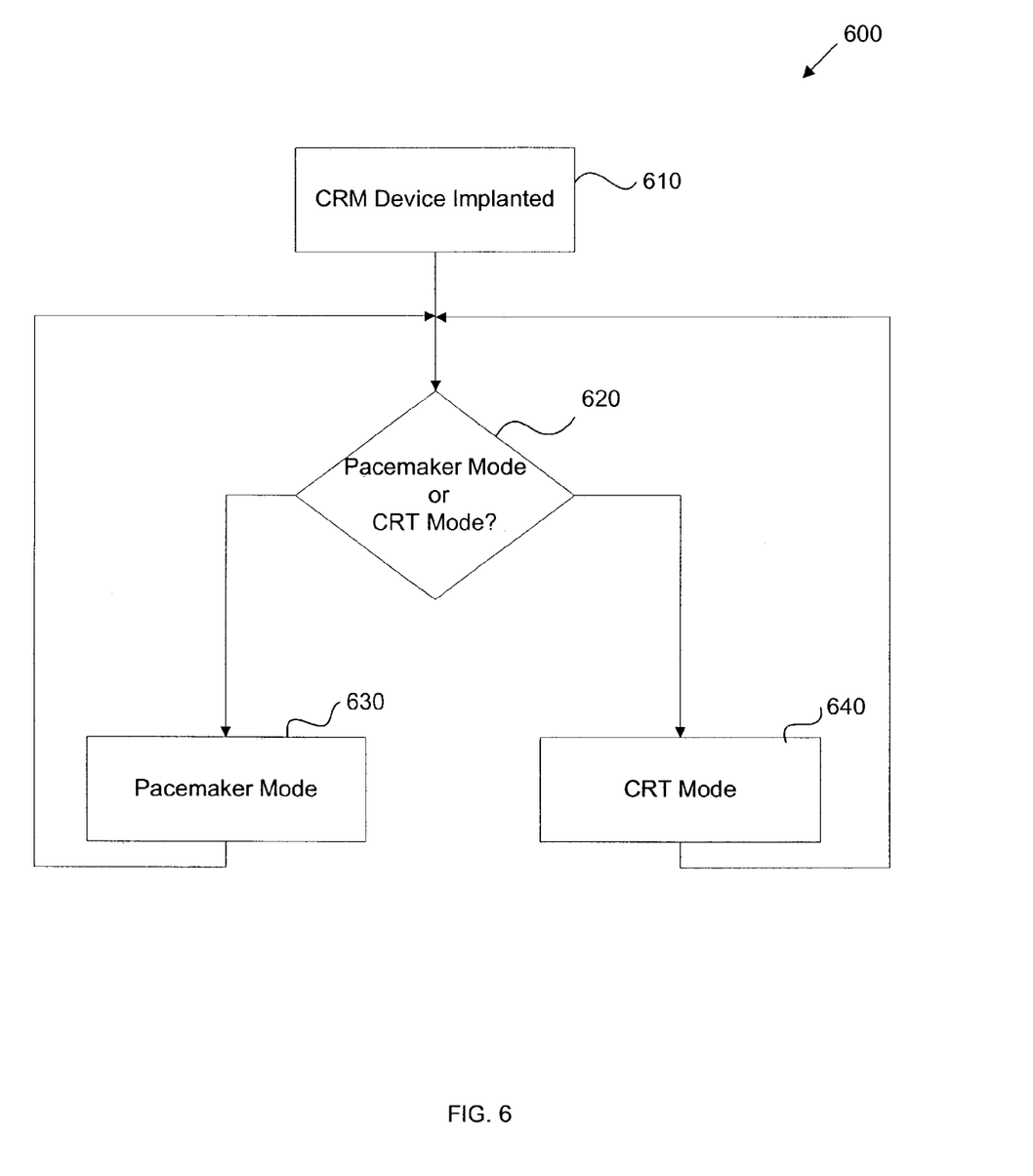
FIG. 6 shows an operational flow of a cardiac rhythm management system according to an embodiment of the present invention.

A method 600 according to another embodiment of the invention is illustrated in FIG. 6. The method 600 is similar to the method 500 illustrated in FIG. 5, except that once the operating mode has been selected by operation 620, control is periodically passed back to operation 620 to make a new determination of the correct operating mode. The device may be set to make this new determination at certain intervals, such as daily or weekly, or the device may be set to make this new determination after a certain event has occurred, such as the failure to sense an intrinsic wave (e.g., an R-wave) after a given interval. In this manner, a CRM system implementing the method 600 periodically reevaluates and adapts to a patient's needs as the patient's needs change. For example, a patient receiving bradycardia pacing support may develop a need for CRT therapy as the patient's needs change. In method 600, the CRM system may automatically detect this change in the patient's needs and switch from pacemaker mode to CRT mode or vice versa.

III. Example Reversion Management System

Another aspect of the invention is a reversion management system. The reversion management system generally includes a protected memory module 360, shown in FIG. 3, to store one or more operating parameters associated with an operating mode. The one or more operating parameters stored in the protected memory module 360 are collectively referred to herein as a reversion mode. During typical CRM system operation, several different environmental conditions may disrupt normal CRM system performance. Such conditions may include high power antennas for radio broadcasting, anti-theft devices used in convenience stores entrances, electrosurgery conducted on the patient, or other such electrical or magnetic interference that may disrupt normal operation. The reversion mode provides the necessary operating parameters associated with the correct operating mode should normal device operation be disrupted.

The protected memory module 360 is a protected memory space based on a specialized hardware design. Typically, an 8-bit memory has a 3-bit parity check associated with it, so that any of the 8-bits can be restored if corrupted. Hamming error correction may also be used to ensure that the memory module 360 is free from corruption.

Figure 7:
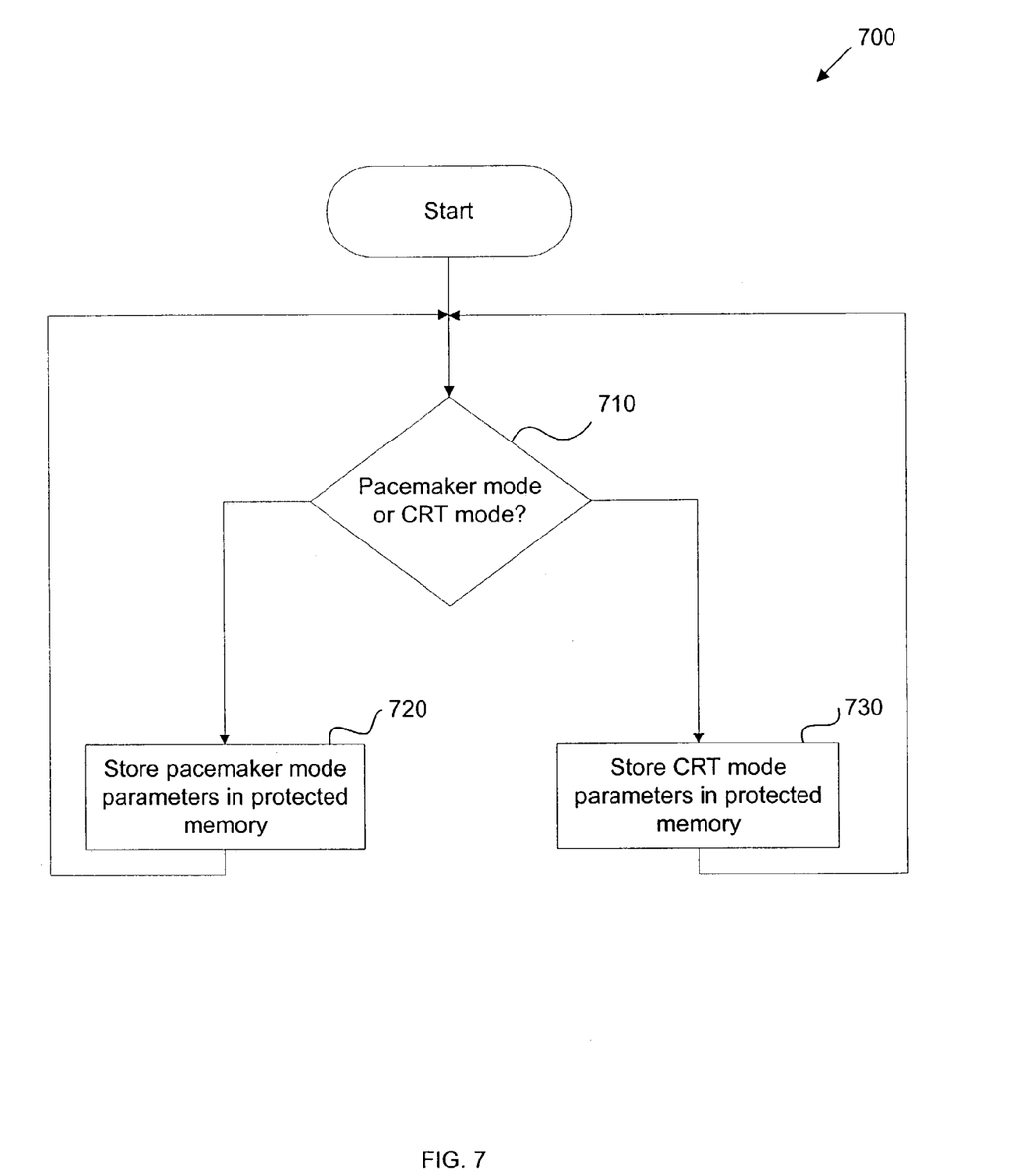
FIG. 7 shows an operational flow of a reversion management subsystem of a cardiac rhythm management system in accordance with another embodiment of the invention.

A method 700 illustrated in FIG. 7 shows an example operational flow for the reversion management system. In operation 710, a CRM system determines whether it is currently operating in pacemaker mode or CRT mode. If the CRM device determines that the operating mode is pacemaker mode, control is passed to operation 720, and the operating parameters associated with the pacemaker mode are stored in a protected memory module. Alternatively, if the CRM device determines that the current operating mode is CRT mode, control is passed to operation 730, and the operating parameters associated with the CRT mode are stored in the protected memory module. The reversion mode stored in the protected memory module may be updated periodically, such as daily or weekly, so that the most current operating parameters associated with the operating mode are stored in the protected memory module.

The operating parameters stored in the protected memory module may be nominal operating parameters associated with a typical pacemaker or CRT device, or may be the actual parameters associated with an operating mode. For example, nominal operating parameters for a pacemaker mode may be sufficient for most patients exhibiting bradycardia because of the rather homogeneous clinical indications associated with bradycardia. Therefore, nominal values may, but need not, be stored in the protected memory as the reversion mode if the device is operating in pacemaker mode. On the other hand, CRT patients typically are not homogenous and therefore require operating parameters adapted individually for each patient. Therefore, actual operating parameters associated with the CRT mode may be stored in the protected memory as the reversion mode.

Figure 8:
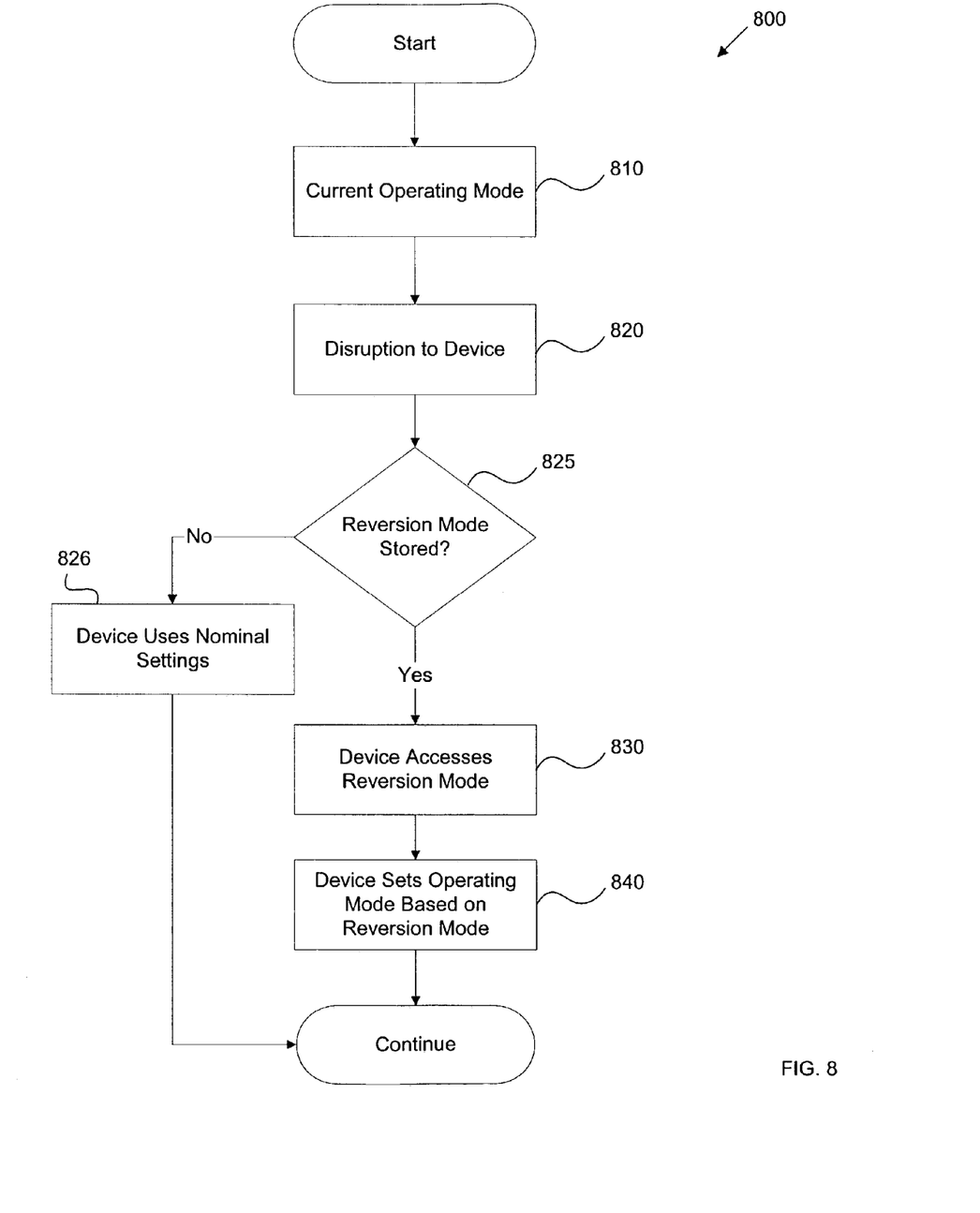
FIG. 8 illustrates an operational flow of a cardiac rhythm management system including a reversion management subsystem in accordance with an embodiment of the invention.

An example operational flow 800 shown in FIG. 8 illustrates how a CRM device may utilize a reversion mode stored in a protected memory to recover from a disruption. In operation 810, the CRM device is functioning normally in an operating mode. In 820, a disruption to the CRM device occurs, such as from one of the external conditions described above. After the CRM device recovers from the disruption, in operation 825 the CRM device determines whether a reversion mode has been stored in the protected memory. If no reversion mode has been stored in protected memory, control is passed to operation 826 and nominal operating parameters are used. However, if a reversion mode has been stored, control is passed to operation 830 and the CRM device accesses the reversion mode stored in the protected memory. Finally, in operation 840, the CRM device resets the operating mode based on the reversion mode to allow the CRM device to function in a manner similar to that before the disruption.

Therefore, in this manner, the CRM device may recover from a disruption and continue to provide beneficial therapy to the patient. The reversion mode allows the CRM device to use the correct operating parameters and continue to operate correctly after a disruption to the CRM device occurs.

The embodiments of the invention described herein may exhibit several advantages over prior devices. The CRM systems disclosed herein provide a plurality of therapy modalities, rather than a single therapy. In this manner, costs associated with product development are reduced. Further, because the CRM system may be reprogrammed while ambulatory to provide different therapies, the device may adapt to a patient's needs as the patient's needs change over time. In addition, because the device is reprogrammable, operating parameters associated with the operating mode may be tailored to provide optimal hemodynamic benefits. Also, a CRM device implemented according to the invention may automatically select the operating mode and thereby reduce or eliminate errors made by a caregiver in the selection of an appropriate operating mode and may continue to provide optimal therapy to the patient even after recovery from a disruption.

The methods of the present disclosure can be implemented using a system as shown in the various figures disclosed herein comprising various devices and/or programmers, including implantable or external devices. Accordingly, the methods of the present disclosure can be implemented: (1) as a sequence of computer implemented steps running on the system; and (2) as interconnected modules within the system. The implementation is a matter of choice dependent on the performance requirements of the system implementing the method of the present disclosure and the components selected by or utilized by the users of the method. Accordingly, the logical operations making up the embodiments of the method of the present disclosure described herein can be referred to variously as operations, steps, or modules. It will be recognized by one of ordinary skill in the art that the operations, steps, and modules may be implemented in software, in firmware, in special purpose digital logic, analog circuits, and any combination thereof without deviating from the spirit and scope of the present invention as recited within the claims attached hereto.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

What is claimed is:

1. A cardiac rhythm management system comprising:
   a cardiac resynchronization therapy module for providing cardiac resynchronization therapy;
   a pacemaker module for providing bradycardia therapy;
   sensing circuitry to collect electrophysiological data indicating the presence or absence of a ventricular conduction delay;
   a selector module coupled to the cardiac resynchronization therapy module and the pacemaker module, wherein the selector module is configured to select an operating mode from among a plurality of operating modes including the cardiac resynchronization therapy module and the pacemaker module;
   wherein the pacemaker module reverts to an asynchronous pacing mode if atrial sensing is lost;
   wherein the cardiac resynchronization module reverts to an inhibited mode in which no pacing pulses are delivered if atrial sensing is lost; and,
   wherein the selector module is configured to automatically select between the cardiac resynchronization therapy module and the pacemaker module based upon the collected electrophysiological data indicating the presence or absence of a ventricular conduction delay.

2. The system of claim 1, wherein the selector module is configured to automatically select between the cardiac resynchronization therapy module and the pacemaker module on a continuous basis.

3. The system of claim 1, wherein the selector module is further configured to compare an interval between a beginning of an intrinsic ventricular depolarization designated as Q* and an ending of the intrinsic ventricular depolarization designated as S* to a threshold in order to automatically select between the cardiac resynchronization therapy module and the pacemaker module.

4. The system of claim 1, wherein the selector module is configured to automatically select between the cardiac resynchronization therapy module and the pacemaker module on a periodic basis.

5. The system of claim 1, wherein the selector module is further configured to:
   detect a time of peak depolarization R in an electrogram waveform;
   derive an interval between a beginning of an intrinsic ventricular depolarization designated as Q* as the point at which a derivative of the electrogram waveform exceeds a specified percentage of the maximum derivative of the electrogram waveform before R;
   derive an ending of the intrinsic ventricular depolarization designated as S* as the point at which a derivative of the electrogram waveform exceeds a specified percentage of the maximum derivative of the electrogram waveform after the depolarization peak; and,
   compare Q* and S* to a threshold in order to automatically select between the cardiac resynchronization therapy module and the pacemaker module.

6. The system of claim 1, further comprising a protected memory module coupled to the selector module, wherein a plurality of operating parameters associated with the operating mode are stored in the protected memory module at a periodic interval.

7. The system of claim 6, wherein the periodic interval is 1 day.

8. The system of claim 6, wherein the periodic interval is 1 week.

9. A method for configuring a cardiac rhythm management system, the method comprising programming the system to automatically:
   (a) detect physiological data of an individual, including electrophysiological data indicating the presence or absence of a ventricular conduction delay; and
   (b) select an operating mode from the plurality of modes for the cardiac rhythm management system based on the physiological data, including selecting between a pacemaker mode and a cardiac resynchronization therapy mode based upon the electrophysiological data indicating the presence or absence of a ventricular conduction delay; and programming the system such that the pacemaker module reverts to an asynchronous pacing mode if atrial sensing is lost, and the cardiac resynchronization module reverts to an inhibited mode in which no pacing pulses are delivered if atrial sensing is lost.

10. The method of claim 9, further comprising programming the system to select between a pacemaker mode and a cardiac resynchronization therapy mode on a continuous basis.

11. The method of claim 9, further comprising programming the system to select between a pacemaker mode and a cardiac resynchronization therapy mode on a periodic basis.

12. The method of claim 9, further comprising programming the system to:
detect a beginning of an intrinsic ventricular depolarization designated as Q*;
detect an ending of the intrinsic ventricular depolarization designated as S*;
measure an interval between Q* and S*; and
compare the interval to a threshold to select the operating mode.

13. The method of claim 12, further comprising programming the system to select a pacemaker mode if the interval is below the threshold.

14. The method of claim 12, further comprising programming the system to select a cardiac resynchronization mode if the interval is equal to or above the threshold.

15. The method of claim 9, further comprising programming the system to:
detect a time of peak depolarization R in an electrogram waveform;
derive an interval between a beginning of an intrinsic ventricular depolarization designated as Q* as the point at which a derivative of the electrogram waveform exceeds a specified percentage of the maximum derivative of the electrogram waveform before R;
derive an ending of the intrinsic ventricular depolarization designated as S* as the point at which a derivative of the electrogram waveform exceeds a specified percentage of the maximum derivative of the electrogram waveform after the depolarization peak; and,
compare Q* and S* to a threshold in order to automatically select between the cardiac resynchronization therapy module and the pacemaker module.

16. The method of claim 9, further comprising programming the system to:
measure a first interval during an intrinsic systolic cycle;
measure a second interval during a stimulated systolic cycle; and
compare a percentage change in a duration between the first interval and the second interval against a threshold to select the operating mode.

17. The method of claim 9, further comprising programming the system to:
measure a first point of an onset of ventricular depolarization;
measure a second point of a peak of a left-ventricular intracardiac electrogram;
calculate an interval based on the first and second points; and
compare the interval to a threshold to select the operating mode.

18. The method of claim 9, further comprising:
measuring a duration of a ventricular depolarization at a surface of the individual; and
comparing the duration to a threshold to select the operating mode.

19. The method of claim 9, further comprising programming the system to:
measure pulse pressures in both a right ventricle and a left ventricle;
calculate a normalized pressure loop area based on the pulse pressures; and
compare the normalized pressure loop area to a threshold to select the operating mode.

20. The method of claim 11, further comprising programming the system to select between a pacemaker mode and a cardiac resynchronization therapy mode on a daily basis.

21. The method of claim 11, further comprising programming the system to select between a pacemaker mode and a cardiac resynchronization therapy mode on a weekly basis.

22. The method of claim 9, further comprising programming the system to perform the steps of
storing a plurality of operating parameters associated with the operating mode in a protected memory at a periodic interval; and
accessing the plurality of parameters upon disruption of the cardiac rhythm management system.

23. The method of claim 22, further comprising setting the periodic interval to 1 day.

24. The method of claim 22, further comprising setting the periodic interval to 1 week.

25. The method of claim 9, further comprising programming the system to perform the step of selecting a first mode from the plurality of modes if a hemodynamic performance of the individual increases through application of cardiac resynchronization therapy.

26. A cardiac rhythm management device comprising:
means for delivering bradycardia therapy in a DDD pacing mode;
means for delivering cardiac resynchronization therapy in a VDD mode;
wherein an AV delay used for cardiac resynchronization therapy is shorter than the AV delay used for bradycardia therapy; and
means for switching from bradycardia therapy to cardiac resynchronization therapy based upon one or more sensed signals that indicate a hemodynamic benefit from cardiac resynchronization therapy.

27. The device of claim 26, further comprising means for storing a plurality of operating parameters to allow the plurality of operating parameters to survive a disruption to the cardiac rhythm management device.

* * * * *